United States Patent [19]

Welter et al.

[11] 4,370,277
[45] Jan. 25, 1983

[54] PHENOXY-CINNAMYL ALCOHOLS

[75] Inventors: Wolfgang Welter; Hilmar Mildenberger, both of Kelkheim, Fed. Rep. of Germany

[73] Assignee: Hoechst Aktiengesellschaft, Frankfurt am Main, Fed. Rep. of Germany

[21] Appl. No.: 315,156

[22] Filed: Oct. 26, 1981

[30] Foreign Application Priority Data

Oct. 28, 1980 [DE] Fed. Rep. of Germany ....... 3040487

[51] Int. Cl.$^3$ .................... C07C 121/75; C07C 43/23
[52] U.S. Cl. ........................... 260/465 F; 260/465 D; 260/544 D; 560/55; 568/441; 568/637; 568/638
[58] Field of Search .................... 260/465 F; 568/638, 568/637

[56] References Cited

U.S. PATENT DOCUMENTS 3,362,997 1/1968 Bolhofer ............................ 568/638
4,118,505 10/1978 Hitamura et al. .................. 424/275

Primary Examiner—Dolph H. Torrence
Attorney, Agent, or Firm—Curtis, Morris & Safford

[57] ABSTRACT

Compounds of the formula:

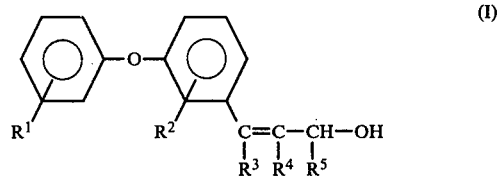

(I)

in which $R^1$ is H, halogen, alkyl or alkoxy; $R^2$ is H, halogen, alkyl or $CF_3$; $R^3$ is H, Cl, Br, alkyl or CN; $R^4$ is H, halogen, alkyl, phenyl or halophenyl; and $R^5$ is H, alkyl, alkinyl or CN; are starting materials for the manufacture of valuable insecticides of the pyrethroid type.

3 Claims, No Drawings

PHENOXY-CINNAMYL ALCOHOLS

Subject of the present invention are phenoxycinnamyl alcohols of the formula:

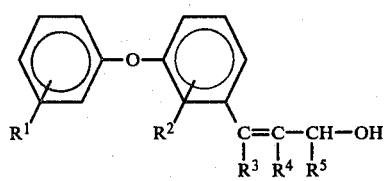

in which:

$R^1$ is hydrogen, halogen, $(C_1-C_4)$alkyl or $(C_1-C_4)$alkoxy, $R^2$ is hydrogen, halogen, $(C_1-C_4)$alkyl or trifluoromethyl, $R^3$ is hydrogen, Cl, Br, $(C_1-C_4)$alkyl or cyano, $R^4$ is hydrogen, halogen, $(C_1-C_4)$alkyl, phenyl or halophenyl, $R^5$ is hydrogen, $(C_1-C_4)$alkyl, $(C_1-C_3)$alkinyl or cyano.

The formula (I) comprises also the different optical and geometrical isomers and the mixtures thereof.

The novel compounds of the formula I are obtained by:

(a) reducing compounds of the formulae:

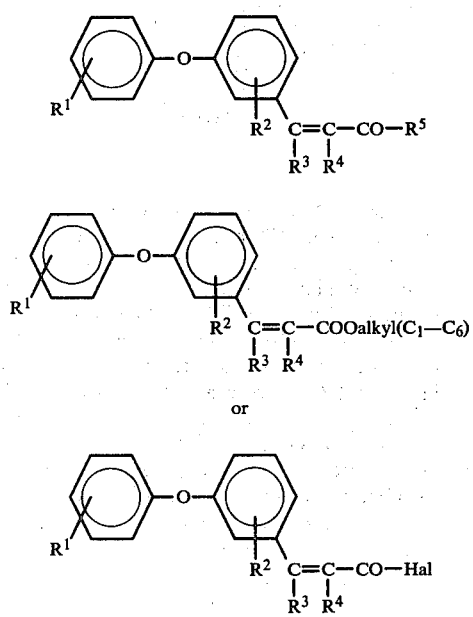

or:

(b) in the case of $R^5$ being CN, treating compounds of the formula (II) with an alkali metal cyanide or an alkaline earth metal cyanide in the presence of an acid, or with trimethylsilyl cyanide; or (c) in the case of $R^5$ being alkinyl, reacting compounds of the formula (II) with a Grignard compound of the formula:

in which $R^6$ is H or $CH_3$.

The variants (a) through (c) for preparing the phenoxycinnamyl alcohols of the formula (I) according to the invention are carried out preferably with the use of suitable solvents or diluents.

Suitable for variant (a) are preferably ethers such as diethyl ether, tetrahydrofuran, dioxan, furthermore hydrocarbons such as toluene and benzene. When sodium borohydride is used as reducing agent, water, alcohols such as methanol or ethanol, nitriles such as acetonitrile or propionitrile may be employed in addition. Suitable for variant (b) are preferably water, alcohols such as methanol, ethanol or ethers such as diethyl ether, tetrahydrofuran, or nitriles such as acetonitrile, while ethers such as diethyl ether, tetrahydrofuran or dioxan are appropriate for variant (c).

As complex metal hydrides for the process variant (a), lithium-aluminum hydride and sodium borohydride are preferably used. Suitable acids for process variant (b) are inorganic acids such as hydrochloric or sulfuric acid, or organic acids such as acetic or formic acid.

The reaction temperature may be varied within wide limits in all three process variants. Generally, the operations are carried out at $-10°$ to $110°$ C.; for variant (a) preferably at $0°$ to $60°$ C., for variant (b) preferably at $-5°$ to $20°$ C., and for variant (c) preferably at $0°$ to $80°$ C.

The reactions proceed generally under normal pressure.

For variant (a), the reactants are preferably used in equimolar amounts; an excess of the one or the other component resulting in no advantage at all. In variant (c) the cyanide, preferably NaCN or KCN, is preferably employed in a 100 to 150% excess.

The products of the process can be worked up in known manner, for example by dilution with water, acidification, extraction with an organic solvent, and separation of the solvent after drying by distillation.

The novel compounds are obtained in the form of oils which can either be distilled or freed from the last volatile components by prolonged heating at moderately elevated temperature under reduced pressure, and thus purified. The refractive index or the boiling point characterizes the compounds.

For the preparation of the likewise novel starting materials of the formulae (II), (III) and (IV), diverse processes are at disposal. The ketones or aldehydes of the formula (II) are for example obtained by reacting in known manner compounds of the formula:

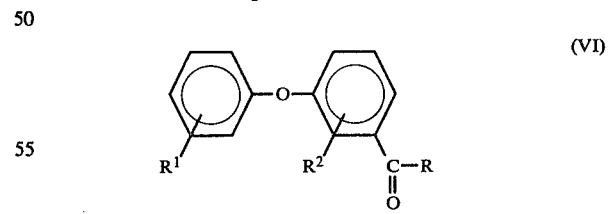

in which R is hydrogen, with keto compounds of the formula:

in the presence of a base and optionally a diluent. A further process consists in reacting trimethylphosphonium salts of the formula:

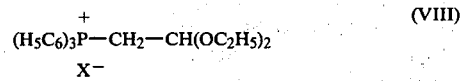

in which X is halogen, with an alkali metal alcoholate at temperatures of from −50° to 100° C., and subsequently hydrolyzing the acetals of the formula:

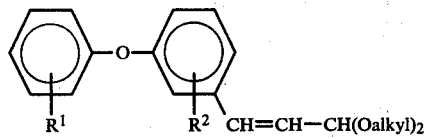

so obtained by means of a strong acid such as hydrochloric acid. Alternatively, the compounds of the formula (II) can be obtained also by reacting compounds of the formula (VI), in which R is lower alkyl, at temperatures of from −50° to 100° C. with a solution of the Vilsmeier-Haack reagent dimethyl formamide/phosphorus oxychloride in dimethyl formamide.

Esters of the formula (III) are for example obtained by reacting aldehydes of the formula (VI)

(a) with carboxylic acid esters, for example ethyl acetate, and an alkali metal alcoholate at temperatures of from 0° to 100° C., or (b) with phosphonic acid esters of the formula:

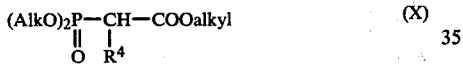

and an alkali metal alcoholate in a lower alcohol, or with sodium hydride in dimethyl formamide or dimethoxyethane.

The acid chlorides of the formula (IV) are prepared by reacting aldehydes of the formula (VI):

(a) with malonic acid in an organic solvent and in the presence of a catalyst such as piperidine, at temperatures of from 20° to 150° C., thereby splitting off water and carbon dioxide, or (b) with acetic anhydride and optionally an alkaline metal acetate as catalyst at temperatures of from 80° to 200° C., and reacting the acids obtained on acidification with a halogenating agent such as thionyl chloride.

The phenoxybenzaldehydes and -ketones of the formula (VI) are known compounds (see German Offenlegungsschriften Nos. 2,624,360, 2,951,496, 2,850,180, 2,709,264 and European Patent Nos. 3,427 and 12,850), or can be synthetized according to known methods [Nachrichten aus Chemie, Technik und Laboratorium 26, 120 (1078)]. The keto compounds of the formula (VII) are also known, as well as the triphenylphosphonium salts of the formula (VIII) and the phosphonic esters of the formula (X).

The compounds of the formula I are valuable starting compounds for the manufacture of pesticidally active substances. By reaction with substituted cyclopropanecarboxylic acids, they yield very efficient insecticides of the pyrethroid type.

EXAMPLE

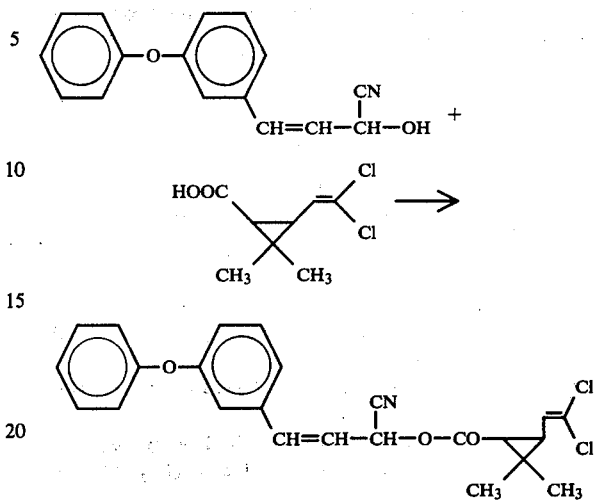

(see copending application Serial No. 315,150 filed October 26, 1981) (German Application P 30 40 488.7 = HOE 80/F 243)

EXAMPLES OF PREPARATION

EXAMPLE

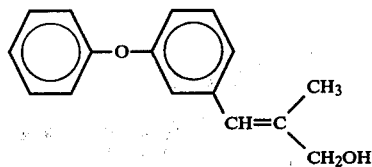

23.8 g (0.1 mol) of 2-methyl-3-(3-phenoxyphenyl)-2-propenal are dissolved in 100 ml of a methanol/ethanol mixture, and 3.8 g (0.1 mol) of sodium borohydride are added portionwise within 30 minutes at 0°–10° C. Agitation is continued for 2 hours at 25° C., the batch is carefully acidified with 2 N sulfuric acid, and the solution is concentrated in vacuo. The remaining mixture is extracted twice with 100 ml of ether each, washed with saturated sodium chloride solution, and dried over sodium sulfate. After having distilled off the ether in vacuo and after distillation, 21.2 g (88% of theory) of 2-methyl-3-(3-phenoxyphenyl)-2-propenol having a boiling point of 161°–166° C./1.3 mbar and a refractive index $n_D^{22} = 1.6015$ are obtained.

EXAMPLE 2

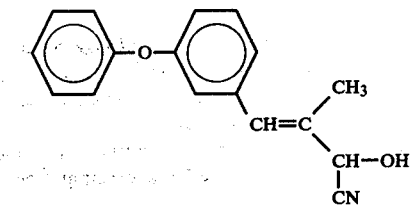

23.8 g (0.1 mol) of 2-methyl-3-(3-phenoxyphenyl)-2-propenal are dissolved in 25 ml of glacial acetic acid, and a solution of 10.2 g of sodium cyanide in 25 ml of water is added dropwise with agitation at 15° C. Subsequently, the batch is stirred for 8 hours at 20° C., poured into 100 ml of water and extracted with 200 ml of ether. The ether phase is washed with dilute sodium bicarbonate solution and saturated sodium chloride solution, and dried over sodium sulfate. After having distilled off the ether in vacuo, 20 g (76% of theory) of 2-hydroxy-3-methyl-4-(3-phenoxyphenyl)-3-butenonitrile having a refractive index $n_D^{21} = 1.6010$ are obtained.

EXAMPLE 3

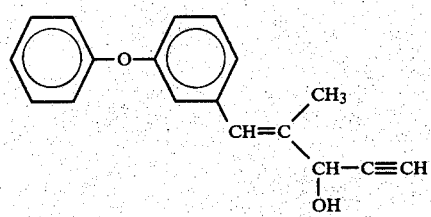

42 g (0.36 mol) of ethyl bromide are added at 30°–40° C. to 7.2 g of magnesium chips in 200 ml of anhydrous tetrahydrofuran, and the batch is then stirred for a further 40 minutes at 50° C. This solution is subsequently added dropwise to a solution saturated at 20° C. of acetylene in 100 ml of tetrahydrofuran, and simultaneously further acetylene is fed in. Dropwise addition being terminated, acetylene is fed in for a further hour. 35.7 g (0.15 mol) of 2-methyl-3-(3-phenoxyphenyl)-2-propenal in 50 ml of anhydrous tetrahydrofuran are added dropwise at 30° C. to the suspension, and the batch is maintained for 4 hours at 40° C. Subsequently, it is cooled to 10° C., poured onto 1,000 ml of icewater, and the precipitate is dissolved with concentrated hydrochloric acid. The batch is then extracted twice with 100 ml of ether each, the ether phase is shaken with water and saturated sodium chloride solution, and dried over sodium sulfate. After removal of the solvent in vacuo, 37.6 g (95% of theory) of 4-methyl-5-(3-phenoxyphenyl)-4-penten-1-in-3-ol having a refractive index $n_D^{26} = 1.6040$ are obtained.

EXAMPLE 4

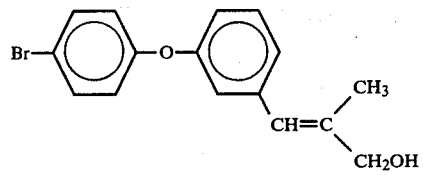

A solution of 10.83 g (0.03 mol) of alpha-methyl-3-(4-bromophenoxy)-cinnamic acid ethyl ester in 50 ml of tetrahydrofuran is added dropwise at 25° C. to 2.5 g of lithium-aluminum hydride in 50 ml of anhydrous tetrahydrofuran. The batch is stirred for 20 hours at 25° C., cooled to 0° C., and icewater is added dropwise until hydrogen development cannot be detected any more. The precipitate is dissolved in 30 ml of concentrated hydrochloric acid, extracted twice with 100 ml of toluene each, and the toluene phase is dried over sodium sulfate. After removal of the solvent in vacuo, 5.26 g (55% of theory) of 2-methyl-3-[3-(4-bromophenoxy)-phenyl]-2-propenol having a refractive index $n_D^{21} = 1.6243$ are obtained.

EXAMPLE 5

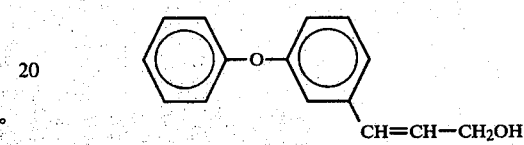

A solution of 51.7 g (0.2 mol) of 3-phenoxycinnamic acid chloride in 50 ml of ether is added dropwise at 10° C. to 4.2 g of lithium-aluminum hydride in 200 ml of anhydrous ether, and the batch is then stirred for 1 hour at 10° C., and for 4 hours at 25° C. It is then cooled to 0° C., icewater is added carefully until no hydrogen develops any more, the precipitate is dissolved with concentrated hydrochloric acid, extracted twice with 200 ml of toluene each, and the organic phase is dried over sodium sulfate. After removal of the solvent in vacuo, 40.4 g (89% of theory) of 3-(3-phenoxyphenyl)-2-propenol having a refractive index $n_D^{23} = 1.6144$ are obtained.

In analogy to one of the Examples 1 to 5, the compounds of the formula (I):

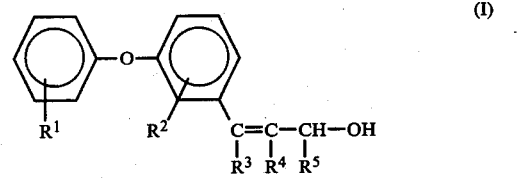

(I)

can be prepared:

| Example | $R^1$ | $R^2$ | $R^3$ | $R^4$ | $R^5$ | refractive index |
|---|---|---|---|---|---|---|
| 6 | H | H | H | H | CN | $n_D^{23} = 1.6089$ |
| 7 | H | H | H | H | C≡CH | $n_D^{24} = 1.5992$ |
| 8 | H | H | H | H | CH₃ | $n_D^{26} = 1.5961$ |
| 9 | 4-Br | H | H | H | H | $n_D^{23} = 1.6390$ |
| 10 | 4-Br | H | H | H | CN | |
| 11 | 4-Br | H | H | H | C≡CH | |
| 12 | 4-Br | H | H | H | CH₃ | $n_D^{23} = 1.6207$ |
| 13 | 4-Cl | H | H | H | H | $n_D^{23} = 1.6250$ |
| 14 | 4-Cl | H | H | H | CN | |
| 15 | 4-Cl | H | H | H | C≡CH | |
| 16 | 4-F | H | H | H | H | $n_D^{24} = 1.6049$ |
| 17 | 4-F | H | H | H | CN | |
| 18 | 4-F | H | H | H | C≡CH | |

-continued

| Example | R¹ | R² | R³ | R⁴ | R⁵ | refractive index |
|---|---|---|---|---|---|---|
| 19 | 4-$CH_3$ | H | H | H | H | $n_D^{23}$ = 1.6101 |
| 20 | 4-$CH_3$ | H | H | H | CN | |
| 21 | 4-$CH_3$ | H | H | H | C≡CH | |
| 22 | 4-$OCH_3$ | H | H | H | H | $n_D^{22}$ = 1.6118 |
| 23 | 4-$OCH_3$ | H | H | H | CN | |
| 24 | 3-Br | H | H | H | H | $n_D^{21}$ = 1.6408 |
| 25 | 3-Cl | H | H | H | H | $n_D^{21}$ = 1.6298 |
| 26 | 3-$CH_3$ | H | H | H | H | |
| 27 | 2-$CH_3$ | H | H | H | H | $n_D^{21}$ = 1.6340 |
| 28 | H | 4-C($CH_3$)$_3$ | H | H | H | $n_D^{25}$ = 1.5943 |
| 29 | H | 4-C($CH_3$)$_3$ | H | H | CN | |
| 30 | H | 4-C($CH_3$)$_3$ | H | H | C≡CH | |
| 31 | H | 4-F | H | H | H | $n_D^{20}$ = 1.6181 |
| 32 | H | 4-F | H | H | CN | |
| 33 | H | 4-F | H | H | C≡CH | |
| 34 | 4-Cl | 4-C($CH_3$)$_3$ | H | H | H | |
| 35 | 4-Cl | 4-C($CH_3$)$_3$ | H | H | CN | |
| 36 | 4-Cl | 4-F | H | H | H | $n_D^{23}$ = 1.6029 |
| 37 | 4-Cl | 4-F | H | H | CN | |
| 38 | 4-$CH_3$ | 4-F | H | H | H | $n_D^{25}$ = 1.5895 |
| 39 | 4-$CH_3$ | 4-F | H | H | CN | |
| 40 | H | H | H | Br | H | $n_D^{22}$ = 1.6270 |
| 41 | H | H | H | Br | CN | |
| 42 | H | H | H | Br | $CH_3$ | $n_D^{23}$ = 1.6121 |
| 43 | 4-Br | H | H | Br | H | |
| 44 | 4-Br | H | H | Br | CN | |
| 45 | 4-Br | H | H | Br | $CH_3$ | |
| 46 | 4-Br | H | H | $CH_3$ | CN | $n_D$ |
| 47 | 4-Br | H | H | $CH_3$ | C≡CH | |
| 48 | H | H | Br | $CH_3$ | H | $n_D^{20}$ = 1.6120 |
| 49 | H | H | Br | $CH_3$ | CN | $n_D$ |
| 50 | 4-Br | H | Br | $CH_3$ | H | $n_D$ |
| 51 | 4-Br | H | Br | $CH_3$ | CN | $n_D$ |
| 52 | H | H | H | $C_2H_5$ | H | $n_D^{27}$ = 1.5894 |
| 53 | H | H | H | $C_2H_5$ | CN | $n_D$ |
| 54 | H | H | H | $C_2H_5$ | C≡CH | |
| 55 | 4-Br | H | H | $C_2H_5$ | H | $n_D$ |
| 56 | 4-Br | H | H | $C_2H_5$ | CN | |
| 57 | H | H | H | $C_6H_5$ | H | |
| 58 | H | H | H | $C_6H_5$ | CN | |
| 59 | H | H | H | –⟨○⟩–Cl | H | |
| 60 | H | H | H | –⟨○⟩–Cl | CN | |
| 61 | H | H | Cl | H | H | $n_D$ |
| 62 | H | H | Cl | H | CN | |
| 63 | 4-Br | H | Cl | H | H | |
| 64 | 4-Br | H | Cl | H | CN | |
| 65 | H | $CF_3$ | H | H | H | |
| 66 | H | H | $CH_3$ | H | H | |
| 67 | H | H | CN | H | H | |
| 68 | H | H | H | Cl | H | |

PREPARATION OF THE STARTING COMPOUNDS

The starting compounds of the formulae II, III and IV can be prepared according to the methods described in Examples (a) to (e).

(a)

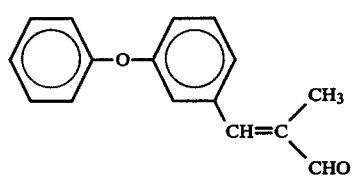

60 ml of 3.6 N sodium hydroxide solution are added dropwise at 0°–10° C. to a solution of 39.6 g (0.2 mol) of 3-phenoxybenzaldehyde and 17.4 g (0.3 mol) of propionic aldehyde in 300 ml of ethanol, and the mixture is stirred at 25° C. for a further 6 hours. Subsequently, the solution is acidified with concentrated sulfuric acid, and concentrated in vacuo. The residue is given into 200 ml of toluene, shaken with water and saturated sodium chloride solution, and dried over sodium sulfate. After removal of the solvent in vacuo and distillation, 40.7 g (86% of theory) of 2-methyl-3-(3-phenoxyphenyl)-2-propenal having a boiling point of 170°–174° C./1 mm Hg, $n_D^{20}$ = 1.6273, are obtained.

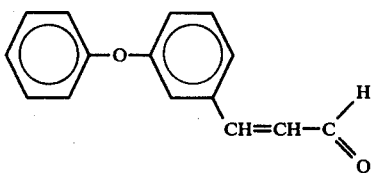
(b)

A solution of 2.3 g (0.1 mol) of sodium in 50 ml of ethanol is added dropwise at 0° C. to a solution of 45.9 g (0.1 mol) of diethoxyethyl-triphenylphosphonium bromide in 200 ml of ethanol. Subsequently, 19.8 g (0.1 mol) of 3-phenoxybenzaldehyde are added dropwise, the batch is maintained at 0° C. for 2 hours and 2 hours at 25° C. After concentration it is extracted with toluene, filtered, dried, and the solvent is distilled off in vacuo. 25.7 g (86% of theory) of 3-phenoxycinnamic aldehyde-diethylacetal are obtained which are heated for 2 hours at 50° C. with 100 ml of 4 N HCl. The batch is extracted twice with 50 ml of ether each, the ether phase is shaken with saturated sodium chloride solution, and dried over sodium sulfate. After having distilled off the solvent in vacuo, and after distillation, 14.5 g (65% of theory) of 3-(3-phenoxyphenyl)-2-propenal, b.p. 150°–160° C./0.3 mm Hg, $n_D^{25}=1.6339$ are obtained.

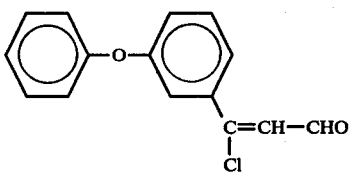
(c)

50 ml of dimethyl formamide are added at 5°–10° C. to 60 g of phosphorus oxychloride, and stirred for a further 30 minutes. Within 1 hour, 42.4 g (0.2 mol) of 3-phenoxy-acetophenone are added at 10° C., and the batch is then stirred for a further 4 hours at 25° C. Thereafter, the solution is shaken onto icewater, and extracted with 200 ml of dichloromethane. The organic phase is shaken with 10% sodium hydroxide solution and water, and dried over sodium sulfate. After removal of the solvent in vacuo, 38.2 g (74%) of 3-chloro-3-(3-phenoxyphenyl)-2-propenal, $n_D^{23}=1.6509$, are obtained.

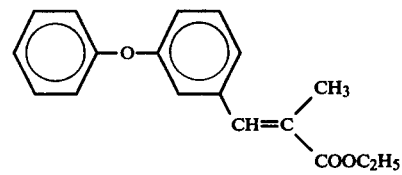
(d)

23.8 g (0.1 mol) of (1-ethoxycarbonylethyl)-diethylphosphonate are added dropwise at 30° C. to a suspension of 3 g of 80% sodium hydride in 60 ml of dimethoxyethane, and agitation is continued for 2 hours at 30° C. At 15° C., a solution of 19.8 g (0.1 mol) of 3-phenoxybenzaldehyde in 50 ml of dimethoxyethane is added dropwise, and agitation is continued for 2 hours at this temperature. The batch is then poured onto 200 ml of water, and extracted twice with 50 ml of ether each, subsequently the ether phase is shaken with saturated sodium chloride solution, and dried over sodium sulfate. After removal of the solvent in vacuo, 22.8 g (81% of theory) of 2-methyl-3-(3-phenoxyphenyl)-2-propenic acid ethyl ester, b.p. 105°–109° C./0.8 mm Hg, are obtained.

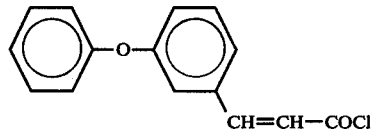
(e)

62.4 g of malonic acid are dissolved in 100 ml of pyridine. After termination of the exothermal reaction, 99 g of 3-phenoxybenzaldehyde and 5 g of piperidine are added, the batch is refluxed for 3 hours, cooled to 25° C. and poured onto ice/concentrated hydrochloric acid in order to wash out pyridine and piperidine, while the acid precipitates in the form of crystals. After drying, 113.7 g (95% of theory) of 3-phenoxycinnamic acid, m.p. 107°–109° C., are obtained. 18 g (0.15 mol) of thionyl chloride are added to a suspension of 24 g (0.1 mol) of 3-phenoxycinnamic acid in 100 ml of toluene, and stirred for 3 hours at 30° C. After removal of the solvent in vacuo, distillation is carried out. 24.6 g (95% of theory) of 3-(2-phenoxyphenyl)-2-propenic acid chloride, b.p. 155°–158° C./0.2 mm Hg, are obtained.

What is claimed is:

1. Phenoxycinnamyl alcohols of the formula:

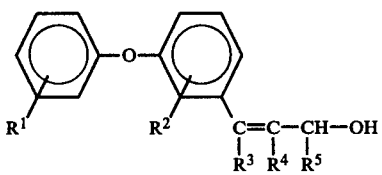
(I)

in which:

R$^1$ is hydrogen, halogen, (C$_1$–C$_4$)alkyl or (C$_1$–C$_4$)alkoxy,

R$^2$ is hydrogen, halogen, (C$_1$–C$_4$)alkyl or trifluoromethyl,

R$^3$ is hydrogen, Cl, Br, (C$_1$–C$_4$)alkyl or cyano,

R$^4$ is hydrogen, halogen, (C$_1$–C$_4$)alkyl, phenyl or halophenyl,

R$^5$ is hydrogen, (C$_1$–C$_4$)alkyl, (C$_1$–C$_3$)alkinyl or cyano.

2. Compounds of the formula I as claimed in claim 1 in the form of their optical enantiomers or their stereoisomers.

3. A phenoxycinnamyl alcohol as defined in claim 1 in which R$^1$ is hydrogen, chlorine, bromine, fluorine, methyl or methoxy; R$^2$ is hydrogen, fluorine, tert-butyl or trifluoromethyl; R$^3$ is hydrogen, bromine, methyl or cyano; R$^4$ is hydrogen, chlorine, bromine, methyl, ethyl, phenyl or chlorophenyl; and R$^5$ is hydrogen, methyl, ethyl, ethinyl or cyano.

* * * * *